United States Patent [19]

Sarnoff et al.

[11] Patent Number: 5,085,641

[45] Date of Patent: Feb. 4, 1992

[54] CONVENIENTLY CARRIED FREQUENT USE AUTO-INJECTOR WITH IMPROVED CAP STRUCTURE

[75] Inventors: Stanley J. Sarnoff, Bethesda; Claudio Lopez, Gaithersburg, both of Md.; N. Lawrence Dalling, Cross Junction, Va.

[73] Assignee: Survival Technology, Inc., Bethesda, Md.

[21] Appl. No.: 507,795

[22] Filed: Apr. 12, 1990

Related U.S. Application Data

[63] Continuation-in-part of Ser. No. 380,459, Jul. 17, 1989.

[51] Int. Cl.⁵ ............................................... A61M 5/20
[52] U.S. Cl. .................... 604/134; 604/135; 604/136; 604/171; 604/220
[58] Field of Search .......... 604/95, 115, 131, 134–136, 604/138, 139, 156–157, 171, 181, 195–196, 220, 137; 401/243

[56] References Cited

U.S. PATENT DOCUMENTS

| 1,204,053 | 11/1916 | Moore | 401/243 |
|---|---|---|---|
| 2,565,081 | 8/1951 | Maynes | 604/136 |
| 2,832,339 | 4/1958 | Sarnoff et al. . | |
| 3,396,726 | 8/1968 | Sarnoff . | |
| 3,403,679 | 10/1968 | Sinclair et al. | 604/137 |
| 3,882,863 | 5/1975 | Sarnoff et al. . | |
| 3,910,260 | 10/1975 | Sarnoff et al. . | |
| 4,004,577 | 1/1977 | Sarnoff . | |
| 4,031,983 | 6/1977 | Kaplan et al. . | |
| 4,168,129 | 9/1979 | Herrnring | 401/243 |
| 4,316,463 | 2/1982 | Schmitz et al. | 604/135 |
| 4,380,403 | 4/1983 | Endres et al. | 401/243 |
| 4,394,863 | 7/1983 | Bartner . | |
| 4,484,910 | 11/1984 | Sarnoff et al. | 604/134 |
| 4,529,403 | 7/1985 | Kamstra . | |
| 4,565,543 | 1/1986 | Bekkering et al. | 604/135 |
| 4,592,745 | 6/1986 | Rex et al. | 604/152 |
| 4,624,660 | 11/1986 | Mijers et al. | 604/136 |
| 4,661,098 | 4/1987 | Bekkering et al. | 604/135 |
| 4,689,042 | 8/1987 | Sarnoff et al. . | |
| 4,755,169 | 7/1988 | Sarnoff et al. . | |
| 4,795,433 | 1/1989 | Sarnoff . | |
| 4,820,286 | 4/1989 | van der Wal . | |
| 4,822,340 | 4/1989 | Kamstra . | |

FOREIGN PATENT DOCUMENTS

0180761  1/1955  Austria ................................ 604/192

Primary Examiner—Stephen C. Pellegrino
Assistant Examiner—Michael Rafa
Attorney, Agent, or Firm—Cushman, Darby & Cushman

[57] ABSTRACT

A stressed spring assembly for providing an operative stroke in cooperating relation with a medicament cartridge assembly of an auto-injector so as to inject a liquid medicament of the medicament cartridge assembly through a hypodermic needle of the medicament cartridge assembly into an injection site of the user. The stressed spring assembly includes a cap structure serving the plural purposes of (1) facilitating the securement of the cap structure and remainder of the auto-injection with the user's pocket, (2) alleviating the likelihood of an unwanted release of the releasable mechanism of the stressed spring assembly with a resultant unwanted movement of the hypodermic needle and an unwanted movement of the liquid medicament outwardly of the hypodermic needle by requiring two different manual movements for its removal, and (3) protecting against an unwanted contact with the hypodermic needle while in extended operative position after withdrawal from the injection site. The cap structure is formed of first and second members disposed in a fixed assembled position with respect to one another into which the first and second members are snap-fitted by a relative movement toward one another in an axial direction. Both members are of a configuration enabling them to be molded by corresponding die surfaces contained on two die members movable together and apart.

24 Claims, 3 Drawing Sheets

CONVENIENTLY CARRIED FREQUENT USE AUTO-INJECTOR WITH IMPROVED CAP STRUCTURE

This application constitutes a continuation-in-part of application Ser. No. 07/380,459, entitled "Conveniently Carried Frequent Use Auto-Injector", filed July 17, 1989.

This application relates to devices for injecting liquid medicaments and, more particularly, to automatic injector types of such devices.

Automatic injectors are well known. Basically, an automatic injector is a device for enabling an individual to self-administer a dosage of a liquid medicament. An advantage of automatic injectors is that they contain a measured dosage of a liquid medicament in a sealed sterile condition capable of storage in such condition for an extensive period of non-use, during which period immediate injection of the stored dosage may be accomplished at any time under the most severe emergency conditions. Another advantage of automatic injectors is that the administration of the self-contained dosage of liquid medicament is accomplished without the necessity of the user initially seeing the hypodermic needle through which the liquid medicament is injected or of manually penetrating such a visible needle into the user's own tissue. Instead, an automatic injector includes a releasable stressed spring assembly. This assembly includes a stressed spring, a releasable mechanism for releasably retaining the spring in a stressed storage position and a releasing mechanism for releasing the releasable mechanism in response to a predetermined actuating procedure.

Automatic injectors have heretofore been particularly suited for use under emergency conditions. For example, many tens of millions of such automatic injectors have been manufactured and sold containing nerve gas antidotes for use under emergency chemical warfare conditions. Typical units which have been utilized for this purpose are disclosed in U.S. Pat. Nos. 2,832,339, 3,882,863, and 4,031,893. In addition, units of this type have been proposed for use in administering antiarrhythmic medicaments under emergency conditions relating to heart attack medical situations. Such use has been in conjunction with portable monitors as is evident from the disclosure contained in U.S. Pat. Nos. 3,910,260 and 4,004,577. It has also been proposed to provide other medicaments useful in treating heart attack symptoms such as clot selective thrombolytic agents (e.g. tPA) and related medicaments. See, for example, U.S. Pat. Nos. 4,689,042, 4,755,169, and 4,795,433. Finally, automatic injectors have been marketed in recent years containing a dosage of epinephrine as an antidote for counteracting severe allergic reactions, as for example, to bee stings and the like.

In all of these instances, the emergency use aspect of the automatic injectors is of primary significance.

The present invention stems from the recognition that the advantages of automatic injectors are not limited only to emergency situations but that there are many other medicinal administration situations requiring a much more frequent usage where the painlessness and simplicity of actuation of an automatic injector combined with other conveniences, would be sufficiently desirable to many individuals to warrant the added costs in comparison with the more simple and less costly manual syringes in widespread use. For example, recently the drug erythropoietin has been approved by the FDA in combating anemia. The drug is particularly useful to kidney patients, aids patients, and patients donating blood for their own use in anticipation of elective surgery. Such patients may have need for the administration of erythropoietin as frequently as once a week. Another example is the recent use of various vasodialators for impotence where injection is made directly in the penis. An automatic injector provides a very convenient way of allowing the patient to administer the liquid medicament without requiring the patient to become proficient in inserting a needle into his own flesh. Under circumstances of this type, it is desirable to provide the user with maximum convenience in availability, handling, and use of the automatic injector while at the same time discouraging use by others, particularly children.

Accordingly, it is an object of the present invention to provide an auto-injector particularly suited to be carried on the person of a user comprising a medicament cartridge assembly, a stressed spring assembly and a tubular housing member mounting the assemblies together in cooperating relation in a storage position with respect to one another so as to provide an exterior housing body structure having a needle extension end and an opposite end and a cap structure extending over the opposite end of the housing body structure. The cap structure and the housing body structure when the assemblies are mounted together in cooperating relation in the storage position defining an exterior configuration of a size and shape approximately the same as that of a conventional fountain pen. The cap structure is of generally tubular construction having an open end and an opposite closed end portion and an elongated clip having one end fixed to the closed end portion of the cap structure. The elongated clip extends longitudinally along the tubular construction of the cap structure and has a free end biased to engage with the exterior of the cap structure adjacent the open end thereof whereby the clip serves to secure the housing cap structure and the housing body structure within a pocket on the person of a user. The medicament cartridge assembly includes a container, a liquid medicament within the container and a hypodermic needle disposed in a storage position and movable therefrom into an extended operative position. The stressed spring assembly includes a spring, a releasable mechanism for retaining the spring means in a stressed storage position and a releasing mechanism operable in response to a predetermined manual actuating procedure to release the releasable mechanism so that spring moves (1) the hypodermic needle into the extended operative position during which the hypodermic needle moves outwardly of the needle extension end of the housing body structure through the skin and into the adjacent tissue of a user and (2) the liquid medicament outwardly through the hypodermic needle into the tissue of the user. The releasing mechanism includes a manually movable member extending beyond the opposite end portion of the housing body structure into an exterior position suitable for manual engagement so as to be manually moved during the manual actuating procedure to which the releasing mechanism is responsive to release the releasable mechanism. The cap structure is detachably secured to the housing body structure (1) in the storage position in open ended telescopic relation with an opposite end portion of the housing body structure covering the manually movable member so as to prevent the manual engagement of the manually movable member without the cap structure being detached from the storage position with respect to the housing body structure and (2) in a final position in open ended telescopic relation with a needle extension end portion of the housing body structure covering the hypodermic needle in the extended operating position thereof after withdrawal from the injection site. The cap structure when in the storage and final positions with respect to the housing body structure serving the plural purposes of (1) facilitating the securement of the cap structure and housing body structure with the user's pocket, (2) alleviating the likelihood of an unwanted release of the releasable mechanism with a resultant unwanted movement of the hypodermic needle and an unwanted movement of the liquid medicament outwardly of the hypodermic needle, and (3) protecting against an unwanted contact with the hypodermic needle while in the extended, operative position thereof after withdrawal from the injection site.

The present invention also has for its object the provision of the several improvement features. These features include the utilization of a plural function cap structure which forms a part of a stressed spring assembly mountable, as by a forward tubular housing member, in cooperating relation with a medicament cartridge assembly. Another feature is the provision of a cap structure of the type described having a lug cooperating with lug engaging surface on the housing member of the assembly requiring a specific compound movement for disengagement.

Another feature is the provision of a cap structure of snap-together two member construction, in which each member is moldable of plastic material with two die members movable toward and away from each other. Another feature includes the provision of a stressed spring assembly which includes a collet member providing spring fingers with free rearward end portions having generally radially extending locking surfaces engaging a generally radially extending locking surface on the housing member of the assembly operable in response to the forward movement of a safety actuating member to flex inwardly to effect spring biased release of the collet member.

These and other objects of the present invention will become more apparent during the course of the following detailed description and appended claims.

The invention may best be understood with reference to the accompanying drawings wherein an illustrative embodiment is shown.

Figures 1, 2:
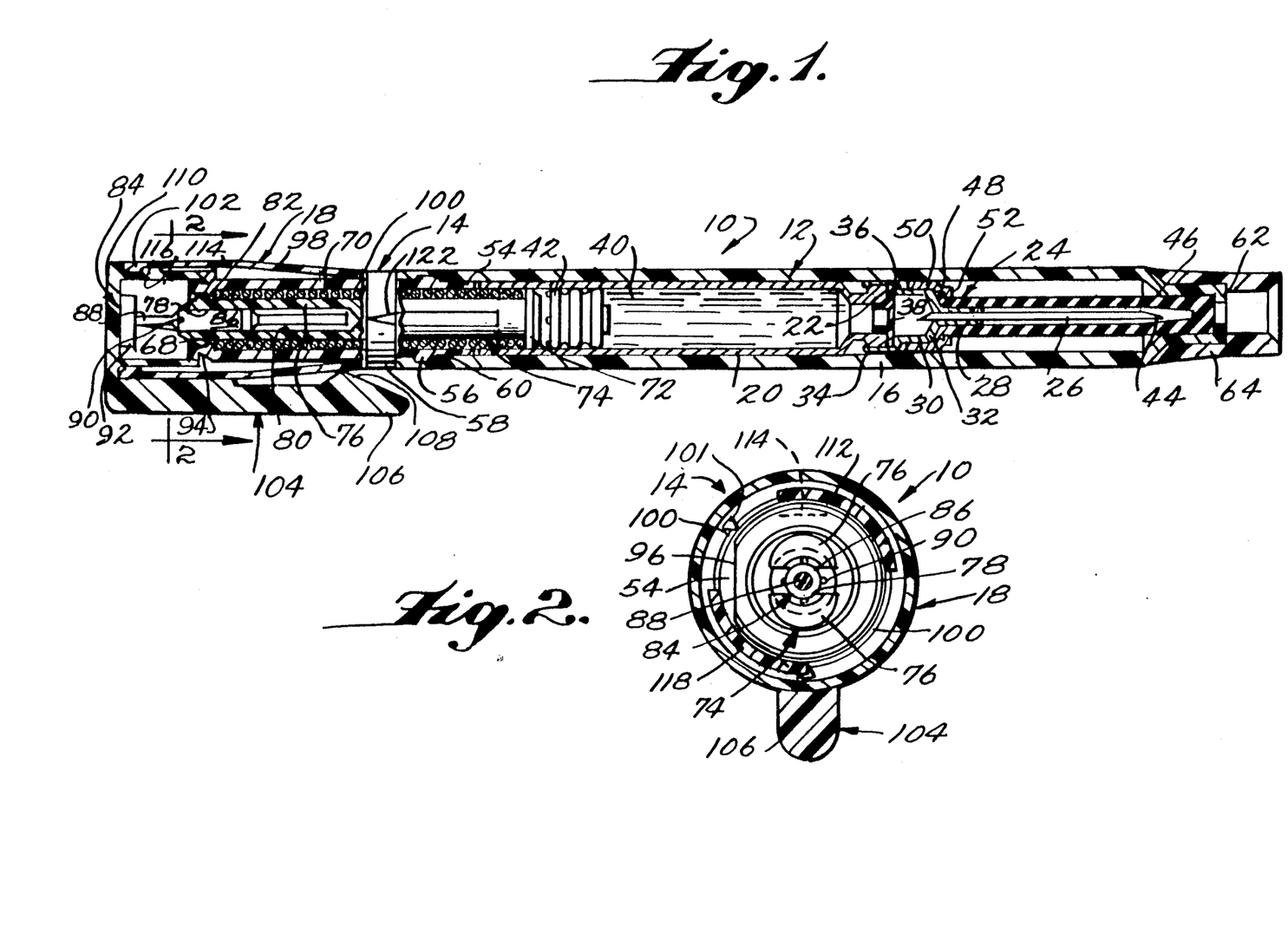
FIG. 1 is a longitudinal sectional view of an auto-injector embodying the principles of the present invention.
FIG. 2 is an enlarged sectional view taken along the line 2—2 of FIG. 1.

Referring now, more particularly, to the drawings, there is shown in FIG. 1 thereof an auto-injector, generally indicated at 10, which embodies the principles of the present invention. The auto-injector includes two basic assemblies: one, a medicament cartridge assembly, generally indicated at 12, and the other, a stressed spring assembly, generally indicated at 14. These two assemblies are mounted in a storage position with respect to one another in a cooperating relation by a means which includes a tubular housing member 16 which serves to receive the medicament cartridge assembly 12 in its forward end and to secure the stressed spring assembly 14 at its rearward end so as to maintain the two assemblies 12 and 14 in their storage position in cooperating relation with one another. The present invention is more particularly concerned with the construction of the stressed spring assembly 14 and, more particularly, the construction and functions attributable to a separable cap structure, generally indicated at 18, forming a part of the stressed spring assembly 14.

The medicament cartridge assembly 12, as shown, is constructed in accordance with commonly assigned concurrently filed application Ser. No. 07/507,850. It will be understood that the stressed spring assembly 14 of the present invention may be utilized in other auto-injector combinations embodying other types of medicament cartridge assemblies. As, for example, cartridge assemblies of the type embodied in Sarnoff U.S. Pat. No. 3,396,726, dated Aug. 13, 1968, in which the needle of the cartridge is disposed within the medicament chamber so that the medicament is moved outwardly of the chamber through the needle as the needle moves into the muscle tissue of the user. Examples of other types of medicament cartridge assemblies include multiple chamber assemblies of the type described in U.S. Pat. Nos. 4,394,863, 4,529,403, 4,820,286, 4,822,340, and commonly assigned concurrently filed application Ser. No. 07/507,756.

The preferred illustrated type of medicament cartridge assembly 12, as shown, includes a generally cylindrical container 20 which preferably is made of glass and has its rear end open and its forward end necked down and formed with an exterior flange 22. A metal hub member, generally indicated at 24, serves to fixedly secure a rearward end portion of a hypodermic needle 26 with the flange 22 of the necked down forward end of the container 20. The hub member 24 includes a crimped down forward portion 28 which sealingly engages the exterior periphery of a rear end portion of the hypodermic needle 26. The hub member 24 includes a central portion 30 which is joined with the forward portion by a forward annular shoulder 32. The central portion 30 provides a sealed hollow interior space into which the rearward end of the needle 26 extends. As shown, the rearward end of the needle is sharpened to present a rearwardly extending point. The hub member 24 also includes a rearward portion 34 which is joined with the central portion by a rearward shoulder 36.

A diaphragm seal 38 has its outer marginal periphery mounted, between the flange 22 of the necked down end of the container 20 and the rearward surface of the rearward shoulder 36 of the hub member 24. The rearward portion 34 of the hub member 24 is crimped over the exterior flange 22 of the necked down forward end of the container 20 to fixedly secure the needle 26 to the container 20.

A liquid medicament 40 is filled within the container 20 so as to be confined forwardly by the diaphragm seal 38 and rearwardly by a plunger or piston 42 which is formed of resilient material with and exterior periphery in sliding sealing engagement with the interior periphery of the container 20 in a position generally forwardly of the rear extremity thereof.

Mounted in surrounding relation to the needle 26, which extends forwardly from the crimped forward portion 28 of the hub member 24 and terminates in a forward sharpened end 44, is a resilient sheath 46. The resilient sheath 46 includes a closed forward end disposed forwardly of the sharpened end 44 of the needle 26 and a rearward end which is shaped to engage over the crimped forward portion 28 of the hub member 24. The rearward end of the sheath 46 is provided with an integral radially outwardly extending annular flange 48. An annular sheath retaining member 50 including an interior flange 52 on one end thereof is engaged on the central portion 30 of the hub member 24 so that its flange 52 engages the flange 48 of the sheath 46 so as to sealingly retain the rearward end of the sheath 46 in abutting engagement with the forward shoulder 32 of the hub member 24.

If desired, and depending upon the amount of liquid medicament included within the container 20, a spacer member (not shown) may be mounted within the rearward end portion of the container 20 rearwardly of the piston 42 in accordance with the teachings of U.S. Pat. No. 4,031,893, the disclosure of which is hereby incorporated into the present specification.

Figure 7:
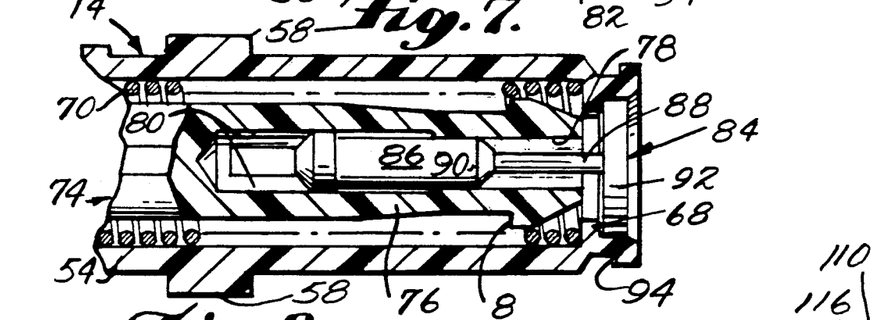
FIG. 7 is a view similar to FIG. 5, showing the position of the parts just after actuation.

The spring assembly 14 which is constructed in accordance with the principles of the present invention includes a main rearward tubular housing member 54 having a forward annular ridge 56 formed on the exterior periphery thereof in rearwardly spaced relation to the forward end thereof and a rearward ridge 58 of slightly greater exterior diameter disposed in rearwardly spaced relation with respect to the forward ridge 56. The forward tubular housing member 16 has its rearward interior periphery formed with an annular groove 60 so as to enable the rearward end portion of the tubular housing member 16 to be moved rearwardly over the forward end portion of the tubular member 54 of the spring assembly 14 so as to be retained therein in a position in which the rearward extremity of the forward tubular housing member 16 engages the forward surface of the rearward annular ridge 58. The forward end portion of the forward tubular housing member 16 is of reduced diameter and has an apertured end wall 62 thereon. An injection site tubular insert 64 is fitted over the reduced end of the forward housing member 14. The insert 64, as shown in FIG. 1, is constructed in accordance with the teachings of commonly assigned U.S. patent application Ser. No. 07/380,451, so as to convert the normally intramuscular injector 10 into a subcutaneous injector. FIG. 7 illustrates an intramuscular type insert 66. For present purposes, the aforesaid application is hereby incorporated by reference into the present specification.

The interior diameter of the reduced portion of the housing member 16 is of a size sufficient to receive the closed forward exterior peripheral extremity of the resilient sheath 46 of the medicament cartridge assembly 12 when the latter is mounted within the rearward open end of the forward housing member 14. It will be noted that the rearward end of the container 20 is disposed in generally abutting relation to the forward extremity of the tubular housing member 54 of the spring assembly 14.

The tubular housing member 54 of the spring assembly 14 is formed with an interior annular flange 68 spaced slightly inwardly from the rearward end thereof. The forward surface of the annular flange 68 is adapted to be engaged by a rearward volute of a coil spring 70 forming a part of the stressed spring assembly 14. The forward volute of the coil spring 70 engages a rearwardly facing surface of a forward flange 72 of a collet member, generally indicated at 74.

The collet member 74 extends rearwardly from the forward flange 72 thereof within the coil spring 70. The rearward end portion of the collet member 74 is split so as to form a plurality (two) of rearwardly extending spring fingers 76. The spring fingers 76 shown are formed with a pair of oppositely facing rearward arcuate surfaces 78 which extend from the rearward extremity thereof inwardly and a pair of forward arcuate surfaces 80 of a slightly greater radius extending forwardly therefrom. The rearward peripheral portion of the fingers 76 are formed with radially outwardly extending arcuate flanges presenting forwardly facing locking surfaces 82 which are adapted to engage along a generally radially extending plane with the rearwardly facing surface of the interior annular flange 68 of the rearward housing member 54. As shown, the locking surfaces 82 are disposed in a radial plane and the rearwardly facing surface of the annular flange 68 has a slight angular extent, as, for example, 16°. It will be noted that the rearward peripheral portions of the fingers 76 also include frustoconical rearwardly and outwardly facing surfaces that cam the fingers 76 within the flange 68 during assembly.

As shown, a safety actuating pin member, generally indicated at 84, is disposed in cooperating relation with the resilient fingers in a storage position and includes a forward portion 86 which is generally coextensive with the rearward arcuate surfaces 78 of the resilient fingers 76. The safety actuating member 84 also includes an intermediate portion 88 of a reduced diameter with respect to the forward portion 86, there being a frustoconical transition between the two portions. Formed on the forward portion adjacent the frustoconical transition is a series of annularly spaced threshold pressure inducing protrusions in the form of semi-spherical knobs 90 extending therefrom. The rearward extremity of the two spring fingers 76 of the collet member 74 are disposed forwardly of the knobs 90 and the forward extremity of the forward pin portion 86 is slightly enlarged to provide a retaining protrusion configured to enter beyond the arcuate surfaces 78 onto the surfaces 80 so as to prevent accidental rearward withdrawal of the safety actuating member 84. Finally, the safety actuating member 84 includes a rearward thumb-engaging or actuating portion 92 of an enlarged diametrical size. The thumb-engaging portion 92 is of a size to engage within a corresponding capturing recess in the rearward interior periphery of the rearward housing member 54 rearwardly of the annular flange 68. It can be seen that when the locking surfaces 82 of the spring fingers 76 are engaged with the rearwardly facing locking surface of the flange 82, the coil spring 70 is retained in a stressed condition between the forward flange 72 of the collet member 74 and the forwardly facing surface of the interior flange 68 of the housing member 54.

The rearward exterior periphery of the housing member 54 is formed with a forwardly spaced annular groove 94 which defines a rearward radially outwardly extending annular flange. As best shown in FIG. 2, a segmental portion of the flange is removed, as indicated at 96, to a radially inward extent equal to the radius of the annular groove 94. The flange thus provided, which has an effective arcuate extent of approximately 300°, serves to permit the housing cap structure 18 to be retained in a storage position within the stressed spring assembly 14.

As shown, the cap structure 18 includes a first tubular member 98 which is preferably molded of a suitable plastic material in a configuration which provides a central axis. The tubular member 98 has a forwardly converging frustoconical section which terminates in a forward interior flange 100 and a rearward generally cylindrical section which terminates in a rearward interior flange 102. As best shown in FIG. 2, extending rearwardly from the forward interior flange 100 within the forward frustoconical section are three equally annularly spaced guide bars 101. The radially inward extent of the rearward flange 102 is slight enabling the first tubular member 98 to be molded by two cooperating die members which are moved into cooperating relation with one another in the axial direction of the central axis provided by the tubular member 98. The two die members can then be separated by axial movement in the opposite direction.

The cap structure 18 also includes a second clip member, generally indicated at 104, which also is preferably molded of a suitable plastic material. As shown, the clip member 104 includes an elongated clip 106 having a forward end formed with a protrusion 108 which extends radially inwardly. Formed integrally with the rearward end of the clip 106 is a mounting section which includes a circular rearward wall portion 110 having an exterior dimension generally equal to the exterior dimension of the cylindrical rearward section of the tubular member 98.

Figure 3:
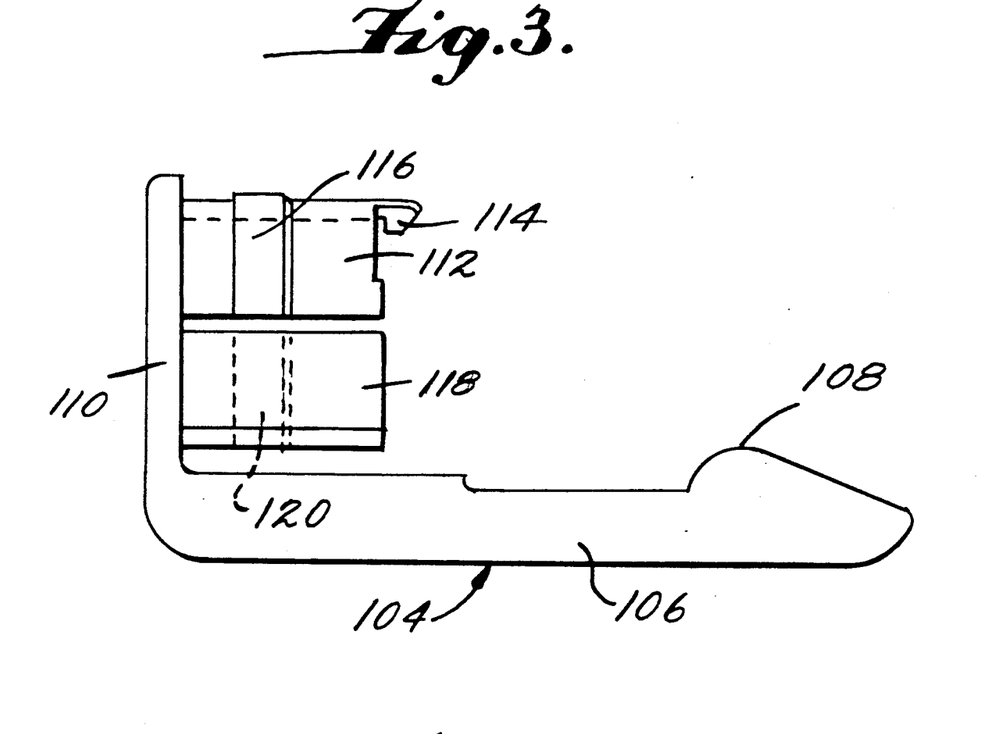
FIG. 3 is a side elevational view of the clip component of the housing cap structure.
Figure 4:
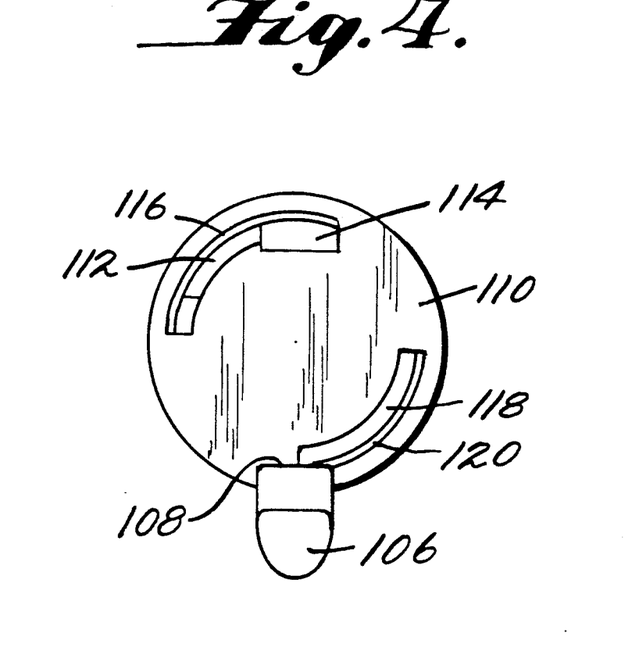
FIG. 4 is a right end view of the clip component shown in FIG. 3.

As best shown in FIGS. 3 and 4, the mounting section of the clip member 104 includes a first arcuate wall portion 112 which extends forwardly from the rearward wall portion 110 and terminates in a radially inwardly extending lug 114 having a rearwardly facing locking surface thereon displaced 180° from the clip 106. The exterior periphery of the first arcuate wall portion 112 includes an arcuate ridge 116 having a sloping forward surface and a rearward abutting edge surface. A second arcuate wall portion 118 extends integrally forwardly from the rearward end wall portion 110 in generally diametrically opposed relation with respect to the first arcuate wall portion 112. The second arcuate wall portion 118 likewise includes an arcuate ridge 120 on its exterior periphery which is bevelled at its forward edge and extends sharply transversely at its rearward edge.

It will be noted that the clip member 104 in the configuration described is capable of being molded by two cooperating die members which are movable toward one another into cooperating relation in a direction perpendicular to the direction of transverse alignment between the lug and clip. After molding has been accomplished, the two die members can be moved apart in the opposite direction to release the clip member 104.

The arrangement of the first and second members 98 and 104 is such that they can be moved and held into an assembled position by a relative movement toward one another in a direction along the axis of the tubular member 98. The rearward interior flange 102 of the cylindrical section of the tubular member 98 engages snugly over the exterior periphery of the two arcuate wall portions 112 and 118 and then the rearward flange 102 thereof rides up and snaps over the two exterior arcuate ridges 116 and 112, thus holding the two members 98 and 104 in assembled relation together.

The cap structure 18 is assembled in a storage position within the stressed spring assembly 14 by engaging the open forward end in telescoping relation over the rearward end portion of the rearward housing member 54. In this regard, it will be noted from FIGS. 1 and 2 that the exterior periphery of the rearward ridge 58 of the housing member 54 has an arrow indicia 122 embossed thereon in an annular position which is displaced 180° from the cut-off portion 96 of the annular flange. The cap structure 18 is secured in its storage position by mapping the rearward inclined surface of the lug 114 over the flange of the housing member 54. In the event that, during the securement of the cap structure 18, the forward end of the clip 106 is aligned with the indicia 122 which has the effect of aligning the lug 114 with the cut-off portion 98 of the flange of the housing member 54, it is then necessary to turn the cap structure so as to bring the rearwardly facing surface of the lug 114 into abutting relation with the forwardly facing surface of the flange defined by groove 94. It will be noted that the lug 114 rides within the annular groove 94 permitting this turning action.

The auto-injector 10 is normally carried by the user by simply slipping the auto-injector in a pocket and clipping it in a manner similar to a conventional fountain pen. In this regard, it will be noted that the auto-injector includes a housing body structure which is defined by the forward housing member 16, the rearward housing member 54 and the insert 64 or 66. The cap structure 18 is normally retained with its open end in telescoping relation over the rear end of this housing body structure by operation of the lug 114. The protrusion 108 of the clip serves to grip the fabric of the pocket so as to retain the auto-injector including the housing structure within the pocket.

Moreover, it will be noted that the engagement of the cap structure 18 on the housing body structure is such as to prevent movement of the safety actuating pin 84. The intermediate portion 88 and thumb-engaging portion 92 thereof extend rearwardly of the housing structure within the cap structure 18, thus requiring removal of the cap structure from the housing body structure before actuation of the automatic injector can take place.

Removal of the cap structure 18 from the housing body structure constitutes the first step in a predetermined manual actuating procedure for actuating the automatic injector 10. In order to remove the cap structure 18, a combination of two manual movements must be carried out. Thus, it is first necessary to turn the cap structure 18 with respect to the housing body structure until the clip 106 is aligned with the indicia 122. When the cap structure 18 has been turned into this position, the lug 114 which is diametrically opposed to the clip 106 will be disposed within the cut-off portion 96 of the flange defined by the groove 94. This enables the user to perform the second movement of the cap structure 18 which is a longitudinal rectilinear movement in a direction away from the housing body structure along its axis.

Figure 5:
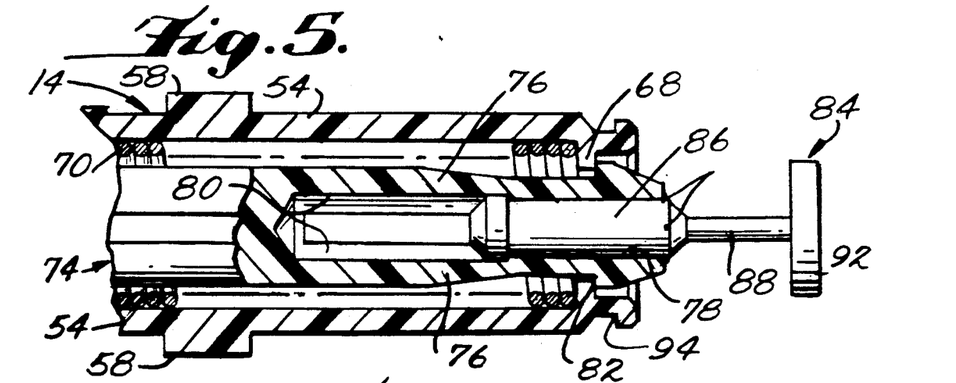
FIG. 5 is an enlarged fragmentary longitudinal sectional view of the rearward end portion of the auto-injector shown in FIG. 1, illustrating the position of the parts after removal of the cap structure.
Figure 6:
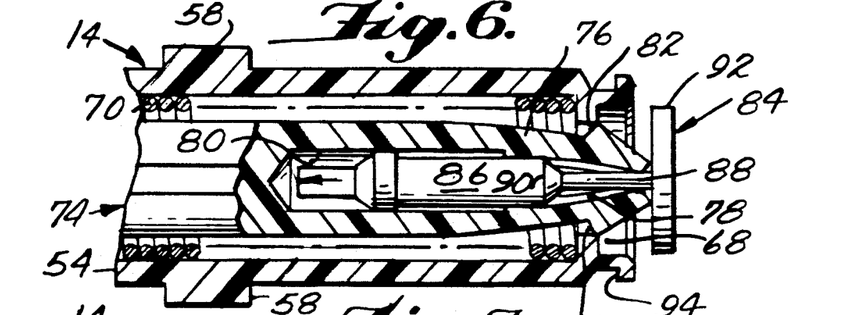
FIG. 6 is a view similar to FIG. 5, showing the position of the parts at the time of actuation.

After the cap structure 18 has been thus removed, the user grasps the forward tubular housing member 16 in one hand and extends the thumb of that hand over the thumb-engaging portion 92 of the safety actuating pin member 84. The user then moves the forward surface of the insert 64 or 66 onto the injection site in engagement with the skin thereof. Next, the safety actuating pin member 84 which is in its storage position, as shown in FIG. 5, is moved forwardly by a thumb pressure sufficient to overcome the threshold pressure provided by the engagement of the knobs 90 with the finger surfaces 76 until the actuating pin member reaches an actuating position, such as shown in FIG. 6. The stress of the spring 70 between the annular flange 68 of the tubular housing member 54 and the forward flange 72 of the collet member 74 urges the forwardly facing locking surface 82 of the spring fingers 76 into engagement with the rearward facing surfaces of the flange 68.

So long as the forward portion 86 of the safety actuating pin member 84 is in the storage position shown in FIG. 5, the spring fingers 76 cannot move transversely inwardly towards one another, thus retaining the locking surfaces in engagement. As soon as the safety actuating pin member 84 reaches the position shown in FIG. 6, the spring fingers flex by virtue of the pressure between the locking surfaces so that their rearward ends move to a position approaching the surface of the intermediate portion 88 adjacent the thumb-engaging portion 92. When the spring fingers have flexed to this extent, the locking surfaces 82 are moved off of the flange 68, allowing the collet member 74 together with the safety actuating pin member 84 to move forwardly under the action of the spring 70.

When the thumb-engaging portion 92 of the safety actuating pin member reaches the flange 68, its movement is stopped and it is captured in the recess within the end of the tubular member 54, as shown in FIG. 7. However, as soon as the locking surfaces 82 have moved forwardly past the flange 68, the spring fingers 76 begin to unflex or move back into their storage position, as shown in FIG. 7. In this position, the collet member 74 continues to move forwardly while the safety actuating pin member 84 is left behind in captured relation by the tubular member 54.

The collet member 74 during its forward movement engages the piston 42 and carries the piston and the entire medicament cartridge assembly 12 forwardly within the housing member 16. During this movement, the sharpened forward end 44 of the needle 26 penetrates the closed end of the rubber sheath 46, passes through the apertured wall 62 and enters the tissue at the injection site. As the forward movement of the container 20, the medicament 40 and the piston 42 move forwardly, the sheath 46 is compressed and, as it compresses, it tends to arrest the movement of the container 20. The continued forward movement of the piston 42 with the collet member 74 pressurizes the liquid medicament 40 causing the diaphragm seal 48 to bulge out and be punctured by the rearward point of the needle 26. The liquid medicament 40 then flows into the central hub portion 30 through the needle 26 and into the tissue at the injection site. The movement of the piston 42 will continue until it reaches the necked down forward end of the container 20.

Figure 8:
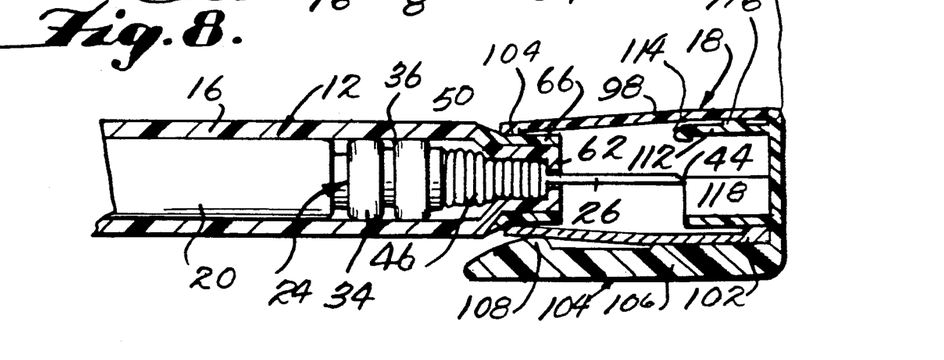
FIG. 8 is an enlarged fragmentary sectional view of the forward end of the auto-injector illustrating the position of the parts after injection and the removable cap structure in its final needle-guarding position.

After the injection has thus been completed, the user withdraws the automatic injector and then places the cap structure 18 over the extended hypodermic needle 26, as shown in FIG. 8, until the inner flange 100 reaches the flared out rearward portion of the insert 66 (or 64). In this way, the cap structure 18 provides the additional function of protecting personnel from engagement with the exposed hypodermic needle 26.

It thus will be seen that the objects of this invention have been fully and effectively accomplished. It will be realized, however, that the foregoing preferred specific embodiment has been shown and described for the purpose of this invention and is subject to change without departure from such principles. Therefore, this invention includes all modifications encompassed within the spirit and scope of the following claims.

What is claimed is:

1. An auto-injector particularly suited to be carried on the person of a user comprising
a medicament cartridge assembly, a stressed spring assembly and means mounting said assemblies together in cooperating relation in a storage position with respect to one another so as to provide an exterior housing body structure having a needle extension end and an opposite end and a cap structure extending over the opposite end of the housing body structure,
said cap structure and said housing body structure when said assemblies are mounted together in cooperating relation in said storage position defining an exterior configuration of a size and shape approximately the same as that of a conventional fountain pen,
said cap structure being of generally tubular construction having an open end and an opposite closed end portion and an elongated clip having one end fixed to the closed end portion of said cap structure,
said elongated clip extending longitudinally along the tubular construction of said cap structure and having a free end biased to engage with the exterior of said cap structure adjacent the open end thereof whereby said clip serves to secure said cap structure and said housing body within a pocket on the person of a user,
said medicament cartridge assembly including means defining a container, a liquid medicament with said container and a hypodermic needle disposed in a storage position and movable therefrom into an extended operative position,
said releasable stressed spring assembly including spring means, releasable means for retaining said spring means in a stressed storage position and releasing means operable in response to a predetermined manual actuating procedure to release said releasable means so that said spring means moves (1) said hypodermic needle into said extended operative position during which the hypodermic needle moves outwardly of the needle extension end of said housing body structure through the skin and into the adjacent tissue of a user and (2) said liquid medicament outwardly through said hypodermic needle into the tissue of the user,
said releasing means including manually movable means extending beyond the opposite end portion of said housing body structure into and exterior position suitable for manual engagement so as to be manually moved during the manual actuating procedure to which said releasing means is responsive to release said releasable means, means between said housing body structure and said cap structure for detachably securing said cap structure on said housing body structure (1) in said storage position in open ended telescopic relation with an opposite end portion of said housing body structure covering said manually movable means so as to prevent the manual engagement of said manually movable means without said cap structure being detached from said storage position with respect to said housing body structure and (2) in a final position in open ended telescopic relation with a needle extension end portion of said housing body structure covering said hypodermic needle in said extended operating position after withdrawal from the injection site, said cap structure when in said positions with said housing body structure serving the plural purposes of (1) facilitating the securement of the cap structure and housing body structure with the user's pocket, (2) alleviating the likelihood of an unwanted release of the releasable means with a resultant unwanted movement of said hypodermic needle and an unwanted movement of the liquid medicament outwardly of the hypodermic needle, and (3) protecting against an unwanted contact with the hypodermic needle while in said extended operative position after withdrawal from the injection site, said assembly securing means including a forward tubular housing member having means on the forward end thereof defining the needle extension end of said housing body structure, said stressed spring assembly including a rearward housing member fixed to said forward housing member defining the opposite end of said housing body structure, said stressed spring assembly also including said cap structure, said means detachable securing said cap structure in said storage position being on said cap structure and said rearward housing member, said manually movable means including an actuating member mounted for movement from a storage position into an actuating position, said predetermined manual actuating procedure to which releasing means is responsive to release said releasable means including a relative movement of said actuating member with respect to said rearward housing member into said actuating position by manually moving the same toward said forward housing member with a thumb which the needle extension end of said housing body structure is retained in an operative position with the skin of the user at the location where the injection is to take place, said container being mounted within said forward tubular housing member for movement from the storage position thereof into an extended position within said forward housing member, said medicament cartridge assembly further including a hub assembly connecting a rearward end of said hypodermic needle with a forward end of said container for movement therewith, a resilient sheath extending over said hypodermic needle when said hypodermic needle is in the storage position thereof, said container having a piston slidably sealingly mounted in a rearward end portion thereof in engagement with the liquid medicament within said container operable to be moved by said spring means into an extended position during which (1) said container is moved into its extended position, (2) said hypodermic needle is moved with said container through said sheath and into the tissue of the user while said sheath is compressed within said forward housing member and (3) said liquid medicament is moved out of said hypodermic needle into the tissue of the user, said hub assembly having a seal therein normally sealing the liquid medicament from contact with said needle operable to burst in response to the initial portion of the movement of said piston within said container.

2. An auto-injector as defined in claim 1 wherein said cap structure comprises a first tubular member having an open end and an opposite end and a tubular axis extending therebetween, a second clip member including an elongated clip and having an attaching portion integral with one end of said elongated clip, a pocket engaging portion integral with an opposite free end of said elongated clip, said first and second members being disposed in a fixed assembled position with respect to one another into which said first and second members are moved by a relative movement toward one another in a direction along said tubular axis and wherein (1) said attaching portion and said pocket engaging portion project from the respective ends of said clip in a direction toward the tubular axis and (2) said attaching portion of said second clip member is secured to the opposite end of said first tubular member, said attaching portion having an integral lug thereon displaced annularly approximately 180° from said clip with respect to said tubular axis and projecting toward said clip, said first tubular member having surfaces defining the entire configuration thereof molded by corresponding die surfaces contained on two die members movable together and apart in directions along said tubular axis, said second member having surfaces defining the entire configuration thereof including a cap mounting surface on said lug facing toward the opposite end of said first tubular member molded by corresponding die surfaces contained on two die members movable together and apart with respect to said second member in a direction generally perpendicular to the direction of projection of said lug toward said clip, said cap mounting surface constituting the means on said cap structure for securing the same to said rearward frame member.

3. An auto-injector particularly suited to be carried on the person of a user comprising a medicament cartridge assembly, a stressed spring assembly and means mounting said assemblies together in cooperating relation in a storage position with respect to one another so as to provide an exterior housing body structure having a needle extension end and an opposite end and a cap structure extending over the opposite end of the housing body structure, said cap structure and said housing body structure when said assemblies are mounted together in cooperating relation in said storage position defining an exterior configuration of a size and shape approximately the same as that of a conventional fountain pen, said cap structure being of generally tubular construction having an open end and an opposite closed end portion and an elongated clip having one end fixed to the closed end portion of said cap structure, said elongated clip extending longitudinally along the tubular construction of said cap structure and having a free end biased to engage with the exterior of said cap structure adjacent the open end thereof whereby said clip serves to secure said cap structure and said housing body structure within a pocket on the person of a user, said medicament cartridge assembly including means defining a container, a liquid medicament within said container and a hypodermic needle disposed in a storage position and movable therefrom into an extended operative position, said releasable stressed spring assembly including spring means, releasable means for retaining said spring means in a stressed storage position and releasing means operable in response to a predetermined manual actuating procedure to release said releasable means so that said spring means moves (1) said hypodermic needle into said extended operative position during which the hypodermic needle moves outwardly of the needle extension end of said housing body structure through the skin and into the adjacent tissue of a user and (2) said liquid medicament outwardly through said hypodermic needle into the tissue of the user, said releasing means including manually movable means extending beyond the opposite end portion of said housing body structure into an exterior position suitable for manual engagement so as to be manually moved during the manual actuating procedure to which said releasing means is responsive to release said releasable means, means between said housing body structure and said cap structure for detachably securing said cap structure on said housing body structure (1) in said storage position in open ended telescopic relation with an opposite end portion of said housing body structure covering said manually movable means so as to prevent the manual engagement of said manually movable means without said cap structure being detached from said storage position with respect to said housing body structure and (2) in a final position in open ended telescopic relation with a needle extension end portion of said housing body structure covering said hypodermic needle in said extended operating position after withdrawal from the injection site, said cap structure when in said positions with said housing body structure serving the plural purposes of (1) facilitating the securement of the cap structure and housing body structure with the user's pocket, (2) alleviating the likelihood of an unwanted release of the releasable means with a resultant unwanted movement of said hypodermic needle and an unwanted movement of the liquid medicament outwardly of the hypodermic needle, and (3) protecting against an unwanted contact with the hypodermic needle while in said extended operative position after withdrawal from the injection site, said assembly securing means including a forward tubular housing member having means on the forward end thereof defining the needle extension end of said housing body structure, said stressed spring assembly including a rearward housing member fixed to said forward housing member defining the opposite end of said housing body structure, said stressed spring assembly also including said cap structure, said means detachable securing said cap structure in said storage position being on said cap structure and said rearward housing member, said manually movable means including an actuating member mounted for movement from a storage position into an actuating position, said predetermined manual actuating procedure to which releasing means is responsive to release said releasable means including a relative movement of said actuating member with respect to said rearward housing member into said actuating position by manually moving the same toward said forward housing member with a thumb which the needle extension end of said housing body structure is retained in an operative position with the skin of the user at the location where the injection is to take place, said releasable means comprising a collet member having a plurality of annularly spaced elongated fingers connected with the rearward end portion thereof for radially inward movement from a collet retaining position into a collet releasing position, said fingers having exterior locking surfaces on outer portions thereof, cooperating locking surface means in said rearward housing member engaging said exterior locking surfaces for (1) retaining (a) said collet member against forward movement and (b) said spring means in stressed condition when said releasable means is in said storage position and (2) for enabling the stressed condition of said spring means to effect (a) radially inward movement of said fingers and (b) forward movement of said collet member in response to the movement of said actuating member into said actuating position.

4. An auto-injector as defined in claim 3 wherein said fingers having interior releasing surface, said actuating member including (1) a forward portion having exterior surface means engaging said interior releasing surfaces when said actuating member is in said storage position, (2) a rearward portion spaced rearwardly of said forward portion for engagement by the thumb of the user, and (3) a slender intermediate portion connected between said forward portion and said rearward portion.

5. An auto-injector as defined in claim 4 wherein said actuating member includes protrusions extending slightly outwardly from the rearward end of said forward portion engageable to provide a slight threshold resistance to movement.

6. An auto-injector as defined in claim 5 wherein said fingers have rear ends free from one another enabling the free rear ends of said fingers to flex inwardly, said locking surfaces and said locking surface means being disposed in a generally radially extending plane when engaged.

7. An auto-injector as defined in claim 6 wherein said cap structure comprises a first tubular member having an open end and an opposite end and a tubular axis extending therebetween, a second clip member including an elongated clip and having an attaching portion integral with one end of said elongated clip, a pocket engaging portion integral with an opposite free end of said elongated clip, said first and second members being disposed in a fixed assembled position with respect to one another into which said first and second members are moved by a relative movement toward one another in a direction along said tubular axis and wherein (1) said attaching portion and said pocket engaging portion project from the respective ends of said clip in a direction toward the tubular axis and (2) said attaching portion of said second clip member is secured to the opposite end of said first tubular member, said attaching portion having an integral lug thereon displaced annularly approximately 180° from said clip with respect to said tubular axis and projecting toward said clip, said first tubular member having surfaces defining the entire configuration thereof molded by corresponding die surfaces contained on two die members movable together and apart in directions along said tubular axis, said second member having surfaces defining the entire configuration thereof including a cap mounting surface on said lug facing toward the opposite end of said first tubular member molded by corresponding die surfaces contained on two die members movable together and apart with respect to said second member in a direction generally perpendicular to the direction of projection of said lug toward said clip, said cap mounting surface constituting the means on said cap structure for securing the same to said rearward frame member.

8. An auto-injector comprising a medicament cartridge assembly, a stressed spring assembly and means mounting said assemblies together in cooperating relation in a storage position with respect to one another so as to provide an exterior housing body structure having a needle extension end and an opposite end and a cap structure extending over the opposite end of the housing body structure, said cap structure and said housing body structure when said assemblies are mounted together in cooperating relation in said storage position defining an exterior configuration of a size and shape approximately the same as that of a conventional fountain pen, said cap structure being of generally tubular construction having an open end and an opposite closed end portion, said medicament cartridge assembly including means defining a container, a liquid medicament within said container and a hypodermic needle disposed in a storage position and movable therefrom into an extended operative position, said releasable stressed spring assembly including spring means, releasable means for retaining said spring means in a stressed storage position and releasing means operable in response to a predetermined manual actuating procedure to release said releasable means so that said spring means moves (1) said hypodermic needle into said extended operative position during which the hypodermic needle moves outwardly of the needle extension end of said housing body structure through the skin and into the adjacent tissue of a user and (2) said liquid medicament outwardly through said hypodermic needle into the tissue of the user, said releasing means including manually movable means extending beyond the opposite end portion of said housing body structure into an exterior position suitable for manual engagement so as to be manually moved during the manual actuating procedure to which said releasing means is responsive to release said releasable means, means between said housing body structure and said cap structure for detachably securing said cap structure on said housing body structure (1) in said storage position in open ended telescopic relation with an opposite end portion of said housing body structure covering said manually movable means so as to prevent the manual engagement of said manually movable means without said cap structure being detached from said storage position with respect to said housing body structure and (2) in a final position in open ended telescopic relation with a needle extension end portion of said housing body structure covering said hypodermic needle in said extended operating position after withdrawal from the injection site, said cap structure when in said positions with said housing body structure serving the plural purposes of (1) alleviating the likelihood of an unwanted release of the releasable means with a resultant unwanted movement of said hypodermic needle and an unwanted movement of the liquid medicament outwardly of the hypodermic needle, and (2) protecting against an unwanted contact with the hypodermic needle while in said extended operative position after withdrawal from the injection site, said container being mounted within said chamber of said housing body assembly for movement from the storage position thereof into an extended position within said chamber of said housing body assembly, said hypodermic needle being connected at a rearward end thereof with a forward end of said container for movement therewith, a resilient sheath extending over said hypodermic needle when said hypodermic needle is in the storage position thereof, said container having a piston slidably sealingly mounted in a rearward end portion thereof in engagement with the liquid medicament within said container operable to be moved by said spring means into an extended position during which (1) said container is moved into its extended position, (2) said hypodermic needle is moved with said container through said sheath and into the tissue of the user while said sheath is compressed within said chamber of said housing body assembly and (3) said liquid medicament is moved out of said hypodermic needle into the tissue of the user.

9. An auto-injector as defined in claim 8 wherein said releasable means comprises a collet member having a plurality of annularly spaced elongated fingers connected with the rearward end portion thereof for radially inward movement from a collet retaining position into a collet releasing position, said fingers having exterior locking surfaces on outer portions thereof, cooperating locking surface means on said rearward housing member engaging said exterior locking surfaces for (1) retaining (a) said collet member against forward movement and (b) said spring means in stressed condition when said releasable means is in said storage position and (2) for enabling the stressed condition of said spring means to effect (a) radially inward movement of said fingers and (b) forward movement of said collet member in response to the movement of said actuating member into said actuating position.

10. An auto-injector as defined in claim 9 wherein said cap structure includes an elongated clip fixed at one end thereof to the closed end portion of said cap structure so that said cap structure serves the further purpose of facilitating the securement of the cap structure and housing body structure with the user's pocket.

11. An auto-injector as defined in claim 10 wherein said means for detachably securing said housing cap structure is operable to enable said housing cap structure to be manually detachable from secured relation with said rearward housing member only by the application of two different manual movement relatively therebetween.

12. An auto-injector as defined in claim 11 wherein the two manual actions enabling said housing cap structure to be manually detached from secured relation with said rearward housing member by said means for detachably securing said housing cap structure comprises a combination of (1) a relative turning movement and (2) a relative longitudinal movement in a direction to move the cap structure and housing body structure apart.

13. An auto-injector as defined in claim 8 wherein said means for detachably securing said housing cap structure is operable to enable said housing cap structure to be manually detachable from secured relation with said rearward housing member only by the application of two different manual movements relatively therebetween.

14. An auto-injector as defined in claim 13 wherein the two manual actions enabling said housing cap structure to be manually detached from secured relation with said rearward housing member by said means for detachably securing said housing cap structure comprises a combination of (1) a relative turning movement and (2) a relative longitudinal movement in a direction to move the cap structure and housing body structure apart.

15. An auto-injector as defined in claim 8 wherein said cap structure includes an elongated clip fixed at one end thereof to the closed end portion of said cap structure so that said cap structure serves the further purpose of facilitating the securement of the cap structure and housing body structure with the user's pocket.

16. A stressed spring assembly for providing an operative stroke in cooperating relation with a medicament cartridge assembly of an auto-injector so as to inject a liquid medicament of the medicament cartridge assembly through a hypodermic needle of the medicament cartridge assembly into an injection site of the user, said stressed spring assembly comprising a tubular housing member having open forward and rearward ends and exterior and interior peripheries extending between said ends, means within a rear end portion of the interior periphery of said tubular member defining an abutment, a coil spring having a rearward end operatively engaged with said abutment and extending forwardly therefrom within the interior periphery of said tubular member, a collet member having an enlarged forward end disposed in operative engagement with a forward end of said coil spring, said collet member extending rearwardly from the forward end thereof within said coil spring and having a rearward end portion split so as to provide a plurality of transversely inwardly deflectable finger portions, cooperating locking surface means on the exterior of said finger portions and a rearward end portion of the tubular member, a safety member mounted in a storage position with respect to said finger portions preventing transversely inward deflection thereof so as to retain the locking surface means thereof in cooperating engagement with the locking surface means of the tubular member when said collet member is disposed in a storage position with respect to said tubular member with said coil spring stressed between said abutment and the enlarged forward end of said collet member, said safety member including a manually engageable free end portion extending rearwardly of said tubular member when said safety member is in said storage position, a cap structure of generally tubular construction having a closed rearward end and an open forward end disposed in a storage position with respect to said tubular member with the open end of said cap structure extending in telescoping relation over a rear end portion of the exterior periphery of said tubular member in enclosing relation with respect to the manually engageable free end portion of said safety member, the interior of said cap structure and the rearward end portion of said tubular member having cooperating surface means thereon (1) normally retaining said cap structure in said storage position with respect to said tubular member and (2) enabling said cap structure to be removed from said storage position with respect to said tubular member to expose the manually engageable free end portion of said safety member, said locking surface means being movable out of cooperating engagement to release the stressed condition of said coil spring to thereby move said collet member through an operative stroke in response to the performance of a predetermined manual actuating procedure which includes (1) a manual removal of said cap structure with respect to said tubular member to expose the manually engageable free end portion of said safety member in the storage position thereof and (2) a manual movement of the manually engageable free end portion of said safety member out of the storage position thereof sufficient to enable the finger portions of said collet member to be deflected transversely inwardly, said locking surface means extend generally in a radial plane when in said cooperative engagement, said finger portions having rear ends free from one another and being of sufficient flexibility to flex inwardly by virtue of the stress of said coil spring so as to move said locking surface means out of cooperative engagement in response to the movement of said safety member out of said storage position.

17. A stressed spring assembly as defined in claim 16 wherein said cap structure comprises a first tubular member having an open end and an opposite end and a tubular axis extending therebetween, a second clip member including an elongated clip and having an attaching portion integral with one end of said elongated clip, a pocket engaging portion integral with an opposite free end of said elongated clip, said first and second members being disposed in a fixed assembled position with respect to one another into which said first and second members are moved by a relative movement toward one another in a direction along said tubular axis and wherein (1) said attaching portion and said pocket engaging portion project from the respective ends of said clip in a direction toward the tubular axis and (2) said attaching portion of said second clip member is secured to the opposite end of said first tubular member, said attaching portion having an integral lug thereon displaced annularly approximately 180° from said clip with respect to said tubular axis and projecting toward said clip, said first tubular member having surfaces defining the entire configuration thereof molded by corresponding die surfaces contained on two die members movable together and apart in directions along said tubular axis, said second member having surfaces defining the entire configuration thereof including a cap mounting surface on said lug facing toward the opposite end of said first tubular member molded by corresponding die surfaces contained on two die members movable together and apart with respect to said second member in a direction generally perpendicular to the direction of projection of said lug toward said clip, said cap mounting surface constituting the cooperating surface means on the interior of said cap structure.

18. A stressed spring assembly for providing an aperture stroke in cooperating relation with a medicament cartridge assembly of an auto-injector so as to inject a liquid medicament of the medicament cartridge assembly through a hypodermic needle of the medicament cartridge assembly into an injection site of the user, said stressed spring assembly comprising a tubular housing member having open forward and rearward ends and exterior and interior peripheries extending between said ends, means within a rear end portion of the interior periphery of said tubular member defining an abutment, a coil spring having a rearward end operatively engaged with said abutment and extending forwardly therefrom within the interior periphery of said tubular member, a collet member having an enlarged forward end disposed in operative engagement with a forward end of said coil spring, said collet member extending rearwardly from the forward end thereof within said coil spring and having a rearward end portion split so as to provide a plurality of transversely inwardly deflectable finger portions, cooperating locking surface means on the exterior of said finger portions and a rearward end portion of the tubular member, a safety member mounted in a storage position with respect to said finger portions preventing transversely inward deflection thereof so as to retain the locking surface means thereof in cooperating engagement with the locking surface means of the tubular member when said collet member is disposed in a storage position with respect to said tubular member with said coil spring stressed between said abutment and the enlarged forward end of said collet member, said safety member including a manually engageable free end portion extending rearwardly of said tubular member when said safety member is in said storage position, a cap structure having a closed rearward end and an open forward end disposed in a storage position with respect to said tubular member with the open end of said cap structure extending in telescoping relation over a rear end portion of the exterior periphery of said tubular member in enclosing relation with respect to the manually engageable free end portion of said safety member, the interior of said cap structure and the rearward end portion of said tubular member having cooperating surface means thereon (1) normally retaining said cap structure in said storage position with respect to said tubular member and (2) enabling said cap structure to be removed from said storage position with respect to said tubular member to expose the manually engageable free end portion of said safety member in response to the manual execution of a combination of two different movements of said cap structure with respect to said tubular member, said locking surface means being movable out of cooperating engagement to release the stressed condition of said coil spring to thereby move said collet member through an operative stroke in response to the performance of a predetermined manual actuating procedure which includes (1) a manual execution of the combination of two movements required to effect removal of said cap structure with respect to said tubular member to expose the manually engageable free end portion of said safety member in the storage position thereof and (2) a manual movement of the manually engageable free end portion of said safety member sufficient to move the safety member out of the storage position thereof enabling the finger portions of said collet member to be deflected transversely inwardly.

19. A stressed spring assembly as defined in claim 18 wherein said locking surface means extend generally in a radial plane when in said cooperating engagement, said finger portions having rear ends free from one another and being of sufficient flexibility to flex inwardly by virtue of the stress of said coil spring and move said locking surface means out of cooperating engagement in response to a forward manual movement of said safety member out of said storage position.

20. A stressed spring assembly as defined in claim 19 wherein said fingers having interior releasing surfaces, said safety member including (1) a forward portion having exterior surface means engaging said interior releasing surfaces when said safety member is in said storage position, (2) a rearward portion spaced rearwardly of said forward portion for engagement by the thumb of the user, and (3) a slender intermediate portion connected between said forward portion and said rearward portion.

21. A stressed spring assembly as defined in claim 20 wherein said safety member includes protrusions extending slightly outwardly from the rearward end of said forward portion engageable to provide a slight threshold resistance to movement.

22. A stressed spring assembly as defined in claim 18 wherein said cap structure comprises
   a first tubular member having an open end and an opposite end and a tubular axis extending therebetween,
   a second clip member including an elongated clip and having an attaching portion integral with one end of said elongated clip, a pocket engaging portion integral with an opposite free end of said elongated clip,
   said first and second members being disposed in a fixed assembled position with respect to one another into which said first and second members are moved by a relative movement toward one another in a direction along said tubular axis and wherein (1) said attaching portion and said pocket engaging portion project from the respective ends of said clip in a direction toward the tubular axis and (2) said attaching portion of said second clip member is secured to the opposite end of said first tubular member,
   said attaching portion having an integral lug thereon displaced annularly approximately 180° from said clip with respect to said tubular axis and projecting toward said clip,
   said first tubular member having surfaces defining the entire configuration thereof molded by corresponding die surfaces contained on two die movable together and apart in directions along said tubular axis,
   said second member having surfaces defining the entire configuration thereof including a cap mounting surface on said lug facing toward the opposite end of said first tubular member molded by corresponding die surfaces contained on two die members movable together and apart with respect to said second member in a direction generally perpendicular to the direction of projection of said lug toward said clip,
   said cap mounting surface constituting the cooperating surface means on the interior of said cap structure.

23. A stressed spring assembly for providing an operative stroke in cooperating relation with a medicament cartridge assembly of an auto-injector so as to inject a liquid medicament of the medicament cartridge assembly through a hypodermic needle of the medicament cartridge assembly into an injection site of the user, said stressed spring assembly comprising
   a tubular housing member having open forward and rearward ends and exterior and interior peripheries extending between said ends,
   spring means carried by said tubular member inwardly of the exterior periphery thereof in a stressed storage position, releasable means for retaining said spring means in said stressed storage position within said tubular member,
   releasing means operable in response to a predetermined manual actuating procedure to release said releasable means so that said spring means moves (1) the hypodermic needle of the medicament cartridge assembly into an extended operative position during which the hypodermic needle moves through the skin and into the adjacent tissue of a user at the injection site and (2) the liquid medicament of the medicament cartridge assembly outwardly through said hypodermic needle into the tissue of the user,
   said releasing means comprising a safety member normally disposed in a storage position including a manually engageable free end portion extending rearwardly of said tubular housing member when said safety member is in said storage position,
   a cap structure having a closed rearward end and an open forward end disposed in a storage position with respect to said tubular housing member with the open end of said cap structure extending in telescoping relation over a rear end portion of the exterior periphery of said tubular member in enclosing relation with respect to the manually engageable free end portion of said safety member,
   the interior of said cap structure and the rearward end portion of said tubular member having cooperating surface means thereon (1) normally retaining said cap structure in said storage position with respect to said tubular member and (2) enabling said cap structure to be removed from said storage position with respect to said tubular member to expose the manually engageable free end portion of said safety member,
   said cap structure comprising a first tubular member having an open end and an opposite end and a tubular axis extending therebetween, and a second clip member including an elongated clip and having an attaching portion integral with one end of said elongated clip, a pocket engaging portion integral with an opposite free end of said elongated clip,
   said first and second members being disposed in a fixed assembled position with respect to one another into which said first and second members are moved by a relative movement toward one another in a direction along said tubular axis and wherein (1) said attaching portion and said pocket engaging portion project from the respective ends of said clip in a direction toward the tubular axis and (2) said attaching portion of said second clip member is secured to the opposite end of said first tubular member,
   said attaching portion having an integral lug thereon displaced annularly approximately 180° from said clip with respect to said tubular axis and projecting toward said clip,
   said first tubular member having surfaces defining the entire configuration thereof molded by corresponding die surfaces contained on two die members movable together and apart in directions along said tubular axis,
   said second member having surfaces defining the entire configuration thereof including a cap mounting surface on said lug facing toward the opposite end of said first tubular member molded by corresponding die surfaces contained on two die members movable together and apart with respect to said second member in a direction generally perpendicular to the direction of projection of said lug toward said clip, said cap mounting surface constituting the cooperating surface means on the interior of said cap structure.

24. A cap structure comprising
a first tubular member having an open end and an opposite end and a tubular axis extending therebetween,
a second clip member including an elongated clip and having an attaching portion integral with one end of said elongated clip, a pocket engaging portion integral with an opposite free end of said elongated clip,
said first and second members being disposed in a fixed assembled position with respect to one another into which said first and second members are moved by a relative movement toward one another in a direction along said tubular axis and wherein (1) said attaching portion and said pocket engaging portion project from the respective ends of said clip in a direction toward the tubular axis and (2) said attaching portion of said second clip member is secured to the opposite end of said first tubular member,
said attaching portion having an integral lug thereon displaced annularly approximately 180° from said clip with respect to said tubular axis and projecting toward said clip,
said first tubular member having surfaces defining the entire configuration thereof molded by corresponding die surfaces contained on two die members movable together and apart in directions along said tubular axis,
said second member having surfaces defining the entire configuration thereof including a cap mounting surface on said lug facing toward the opposite end of said first tubular member molded by corresponding die surfaces contained on two die members movable together and apart with respect to said second member in a direction generally perpendicular to the direction of projection of said lug toward said clip.

* * * * *